United States Patent [19]

Hutson et al.

[11] Patent Number: 5,588,564
[45] Date of Patent: Dec. 31, 1996

[54] EYE SPRAY MIST DISPENSER

[76] Inventors: Clifford L. Hutson, 4440 J Shadow Hills Cir., Santa Barbara, Calif. 93105; Robert Demangus, 1715 N. Pacific Ave., Glendale, Calif. 91202-1108

[21] Appl. No.: 518,143

[22] Filed: Aug. 21, 1995

[51] Int. Cl.$^6$ .......................................... B67D 5/40
[52] U.S. Cl. ....................... 222/383.1; 222/523; 222/525; 604/301
[58] Field of Search ................................. 222/383.1, 523, 222/525, 526, 527; 604/289, 294, 295, 298, 300, 301, 302

[56] References Cited

U.S. PATENT DOCUMENTS

| | | | |
|---|---|---|---|
| 2,320,070 | 5/1943 | Derham et al. | 604/295 |
| 3,910,618 | 10/1975 | Massenz | 604/294 X |
| 4,257,417 | 3/1981 | Gibilisco | 604/302 |
| 4,733,802 | 3/1988 | Sheldon | 604/302 X |
| 4,792,334 | 12/1988 | Py | 604/301 |
| 5,030,214 | 7/1991 | Spector | 604/289 X |
| 5,037,406 | 8/1991 | Smith et al. | 604/301 |
| 5,201,726 | 4/1993 | Kirkham | 604/294 |

*Primary Examiner*—Joseph Kaufman
*Attorney, Agent, or Firm*—Michael G. Petit

[57] ABSTRACT

A device including an eye cup portion affixed to one end of an extendible tube portion, the other end of the tube portion is adapted for releasably attaching the tube portion to the nozzle of a spray-mist fluid dispenser. In combination, the device and mist dispenser are operable for controlling the delivery of a fluid to the eye. The device functions both as mask to confine the distribution of the spray mist ejected from the nozzle upon the eye and as a jig operable for adjusting the distance between the mist dispenser nozzle and the eye cup portion of the device. In operation, with the device affixed to a spray mist dispenser nozzle and the tube portion unextended (nozzle closest to the eye), a dense mist is delivered to the cornea and surrounding eye tissues when mist is dispensed. When the tube portion is extended, the spray mist dispenser nozzle is further from the eye cup thereby reducing the density of the spray mist impinging on the eye. The tube portion of the device includes inner and outer concentric tubes and a conical containment chamber affixed to the outer tube and disposed within the eye cup portion of the device. The distance between the wide end of the eye cup and the nozzle engaging end of the tube portion is telescopically adjustable. The containment chamber may be removed from the device to permit the spray nozzle to be positioned nearer the eye. When the tube portion is unextended, the fluid spray mist impinges on the anterior surface of the eye with the greatest force and concentration. For a gentler, finer delivery of spray mist, the containment chamber is preferably employed and the distance between the dispenser's nozzle delivery orifice and the eye cup portion adjusted and set for comfort and accurate dosimetry.

5 Claims, 3 Drawing Sheets

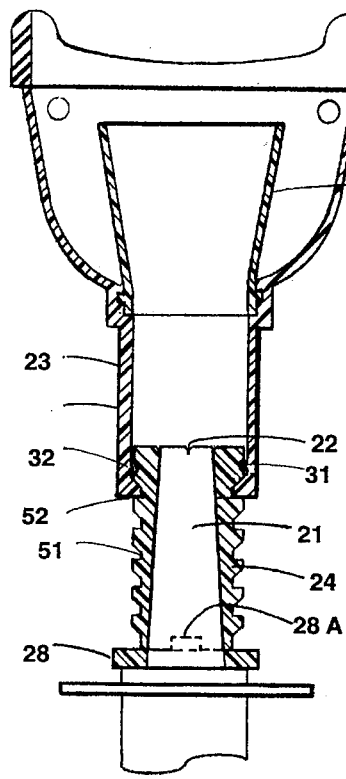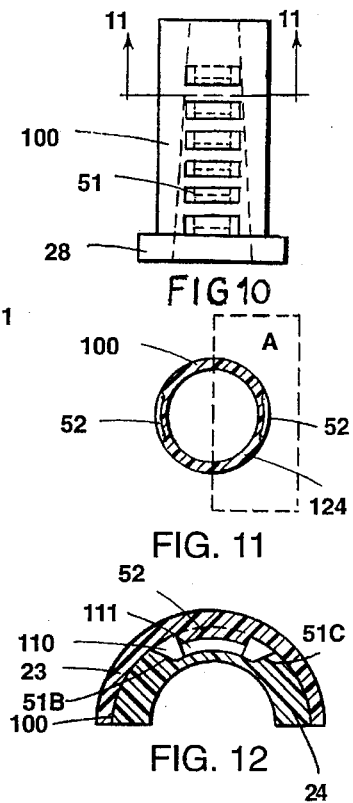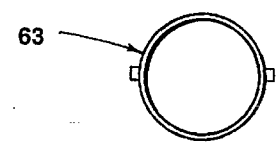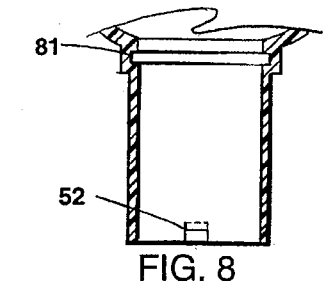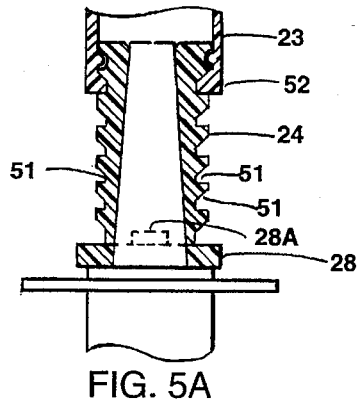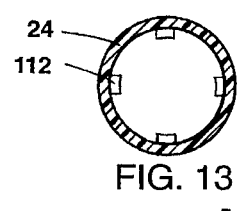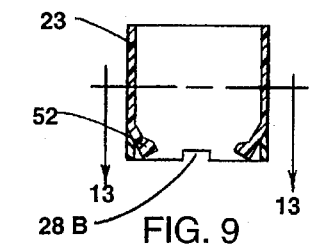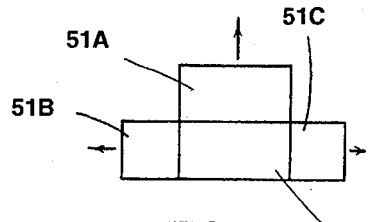

EYE SPRAY MIST DISPENSER

BACKGROUND OF THE INVENTION

1. Field of the Invention

This invention relates to a device for topically administering a fluid to the eye and, more particularly, to a device for controlling the self-administered delivery of a fluid spray mist to the eye.

2. Prior Art

Eye treatment solutions are normally self-administered by using either an eye cup or a dropper. The rim of the eye cup is configured to fit snugly against the soft tissue surrounding the eye. Because of the eye cup rim's mating anatomical design, the rim forms a positive seal when placed over the eye and gently pressed against the infra-orbital tissue. In operation, a fluid such as an eye wash solution is placed in the eye cup and the cup is held against the infra-orbital tissue of the eye. The head is tilted back to allow the solution to immerse the eye. The head may also be moved from side to side to allow the solution to be fully distributed over the cornea and the peripheral tissues of the eye.

Another popular device for self-administering a fluid to the eye is a eye dropper. The eye drop solution is delivered directly into the eyes from either a dropper or a dropper type bottle. The person is usually lying down or has the head leaning back during administration. When using the dropper method of administration, one hand of the user pulls the lower lid away from the eye to expose the conjunctiva so that one or more drops of the solution can be introduced thereonto.

While most people can manage either the eye cup immersion or the eye drop method for the self-administration of a fluid to the eye, there is a segment of the population which find these devices and methods awkward or difficult to perform because of various visual and/or physical limitations. For example, individuals having partial or impaired vision, neuromuscular problems, muscular and/or skeletal disease, and those lacking hand/wrist coordination would fall into this group.

In addition to people having serious eye disorders requiring chronic delivery of medication, there are others suffering from eye irritation of a more temporary nature due to exposure to common irritants in both the home and the work place. The most common irritants such as dust and air laden chemicals, industrial particles, smoke, smog, pollen, and chlorinated water, all cause various degrees of eye irritation resulting in much discomfort to the individual. People troubled by dry eyes may also benefit from using an atomized eye wash solution for eye hydration. Such individuals require eye hydration on a frequent and chronic basis in order to attain a degree of eye comfort. In view of the foregoing, there is a need for a spray mist dispenser enabling the controlled and adjustable delivery of a fluid to the eye which is easy to self-administer, even for handicapped people, and does not require the user to assume a recumbent position to effect self-administration.

SUMMARY OF THE INVENTION

In view of the foregoing limitations of present devices for self-administering a fluid to the eye, it is a primary object of this invention to provide an eye solution mist dispenser device which is easy to use and acceptable to a wide range of users, even those with physical and visual limitations.

It is another object of the invention to provide a device as above which is simple in construction and adapted to matingly and releasably attach to and engage the spray nozzle of prior art spray mist atomizers.

It is a further object of the invention to provide a device for controlling the distribution pattern of a fluid mist delivered to the surface of the eye.

It is yet another object of the invention to provide an eye spray mist device which delivers an adjustable and repeatable dose of medicament to the surface of the eye.

One or more of the following embodiments of the present invention satisfies the foregoing objectives. The device has a tube portion comprising concentric inner and outer robes. The inner tube (alternatively) referred to as an "inner sleeve" herein), slides coaxially and telescopically within the outer tube (or alternatively, outer sleeve) and has one end adapted to matingly engage the (usually male) nozzle of a spray mist dispenser such as those currently employed for the nasal administration of drugs. Such prior art spray mist dispensers (for example, the 12H AFRIN® nasal spray pump, Schering Plough Health Care Products, Inc., Memphis, Tenn.) are manually operated by the user and designed to prevent aspiration of contaminated fluids or particles back into the dispenser's treatment solution reservoir. For example, if the spray dispenser's delivery nozzle is tapered, as is the case with most prior art spray mist dispenser nozzles, the interior wall of the end of the inner sleeve attaching to the nozzle (the dispenser end) is preferably tapered to matingly conform to and snugly receive the nozzle of the spray mist dispenser. At the dispenser end of the outer sleeve, two flexible tabs have a portion projecting inwardly are operable for locking engaging mating notches on the outer surface of the inner sleeve to set the length of the telescopically or slidingly adjustable robe portion according to the degree of intensity of the eye spray mist required.

Providing the device with a tube portion having an adjustable length allows the device to function as a jig for adjusting and setting the distance between the spray mist dispenser's delivery nozzle and the rim of the eye cup portion. When the device is attached to a dispenser nozzle, extension of the tube portion moves the nozzle orifice further away from the eye cup portion and thus, when in use, the eye. Once the desired extension of the tube portion is reached, the tabs affixed thereto are locked in position by rotating the outer sleeve until the elastically flexible tabs engage a correspondingly spaced pair of mating notches on the inner sleeve. Readjustment of the length of the tube portion of the device is accomplished by rotating the outer tube either to the fight or to the leer until the tabs disengage from the notches on the inner tube, then sliding the outer tube to a new extension followed by a second rotation to engage the tabs with a new pair of notches. The device, when used in combination with a spray mist dispenser, enables the use of the spray mist dispenser to self-administer fluids such as eye wash solution to the eye. The compact size and ease of operation of the device makes it particularly useful for self-administration of fluids to the eye by individuals having physical and visual limitations.

The features of the present invention believed to be novel set forth with particularity in the appended claims. However, the invention itself, both as to organization and method of operation together with further objects and advantages thereof may be best understood by reference to the following description taken in conjunction with the accompanying drawings in which:

BRIEF DESCRIPTION OF THE DRAWINGS

FIG. 5 is a vertical cross-sectional view of the embodiment of FIGS. 1 and 2 in accordance with the present invention showing the inner sleeve of the tube portion of the device attached to and matingly engaging the spray nozzle of a prior art dispenser.

FIG. 5A is an enlarged view of the tube portion showing a tab on the outer sleeve engaging a notch or detent rest on the inner sleeve.

FIG. 6 is a cross-sectional vertical view of the spray mist containment chamber.

FIG. 6a is a top view (in the direction of the broad arrow 6a in FIG. 6) showing the anatomically conforming shape of the delivery end of the chamber.

FIG. 7 is a bottom view of the spray mist chamber.

FIG. 8 is a vertical cross-sectional view of the outer sleeve of the tube portion showing the flexible tabs which engage the notches on the concentric inner sleeve of the tube portion of the device.

FIG. 9 is a vertical cross-sectional view of a portion of the outer tube showing the flexible detent tabs projecting inwardly when relaxed.

FIG. 10 is a perspective front view of the inner tube showing with the notches which function as detent rests for the tabs.

FIG. 11 is a cross-sectional view of the inner tube of FIG. 10, taken along section line 11—11 showing the flexible detent tabs engaging the detent rests.

FIG. 12 is an enlarged view of the boxed portion of FIG. 11.

FIG. 13 is an end view of the portion of the inner sleeve which matingly engages the nozzle of a prior art dispenser.

FIG. 14 is a side view of a notch or detent rest.

DESCRIPTION OF THE PREFERRED EMBODIMENTS

Figure 1:
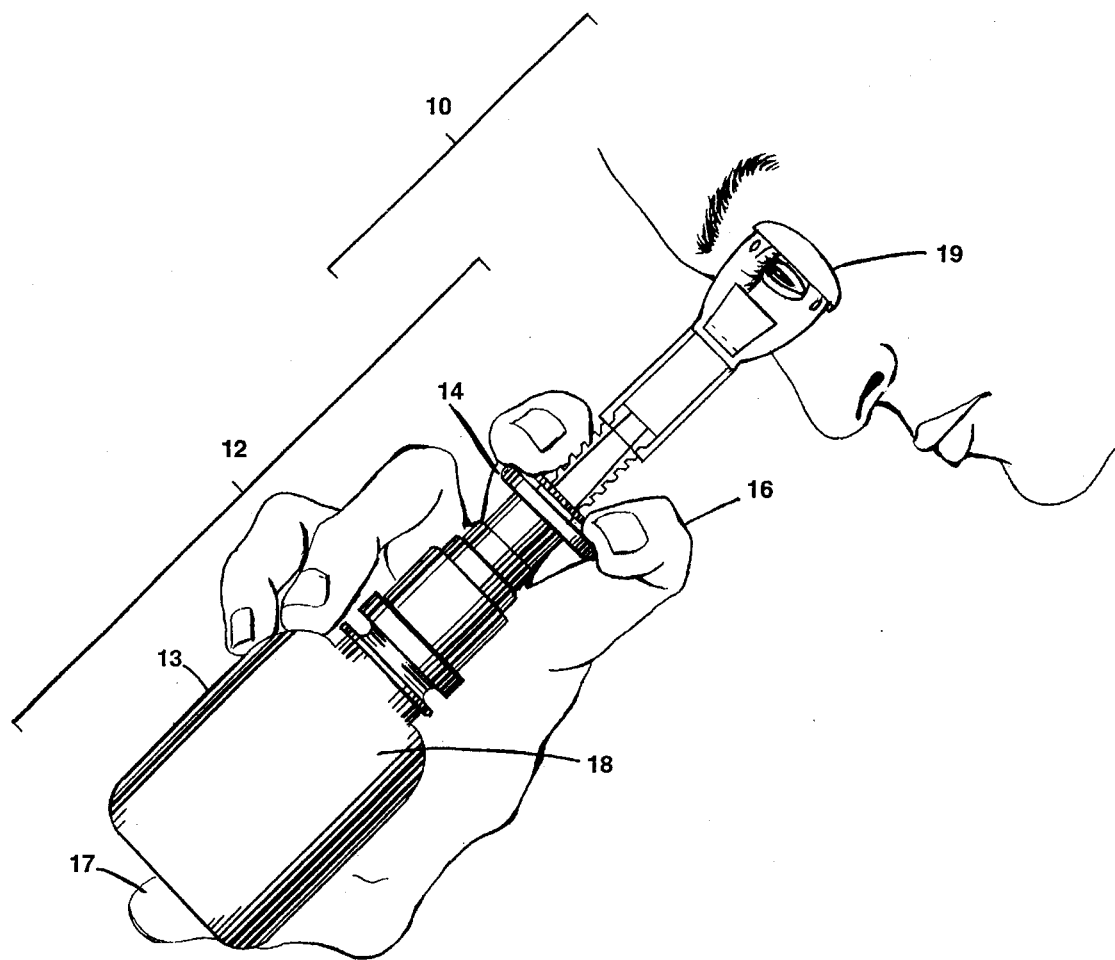
FIG. 1 is a perspective view of a preferred embodiment of the present invention.

A preferred embodiment of the device of the present invention is shown in FIG. 1. The device 10, which may alternately be referred as a spray mist dispenser shield, is shown assembled and removably attached to the delivery tube or of a prior art hand pump type spray mist dispenser 12 (which may be alternatively referred to herein as an "atomizer", a "micromizer" or an "aerosol dispenser"), which dispenser may be releasably attached to a refillable fluid container 13. In FIG. 1, the tube portion of the device 10 is shown in its fully extended position. In operation the eye cup portion 11 of the device 10 is placed over the user's infra-orbital area 19 and is held in position with the thumb 17 of the person's right hand placed under the solution container 13 and with the first finger 16 and second finger 16 placed on the pump activator flange 14. When finger pressure is applied by the fingers to the pump activator flange 14, a spray mist is expelled through an escape orifice 22 in the nozzle or delivery tube 21, thereafter to pass through the inner and outer tube assembly 23 and through the eye cup 11.

When the device is fully extended, this action provides for a fine spray mist treatment solution to be delivered to the eye.

Figure 2:
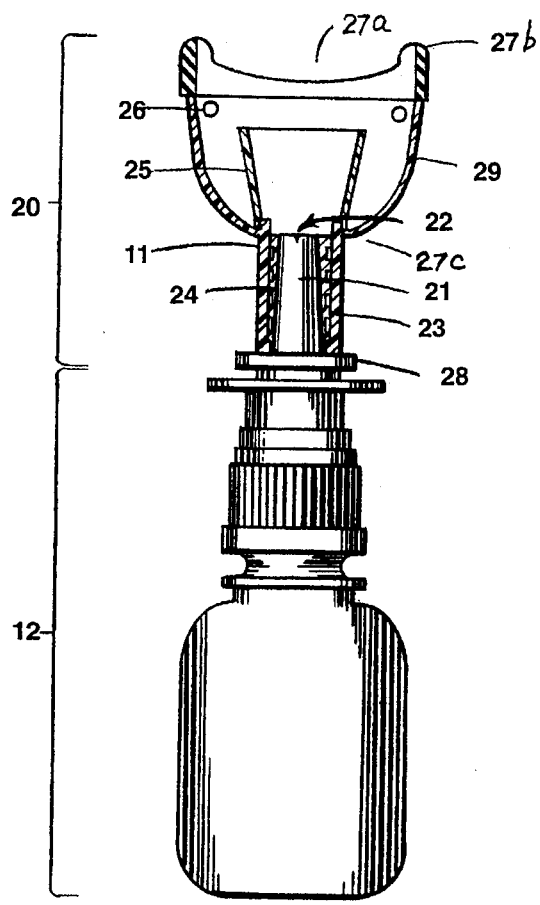
FIG. 2 is a partially cutaway side view of the embodiment of FIG. 1 showing the attachment of the device to a (prior art) aerosol dispenser.

A partial side view of a preferred embodiment of the present invention is shown in FIG. 2. The device 20 is shown in releasable mating engagement with the nozzle 21 of a (prior art) aerosol dispenser 12. The device 20 is shown with the tube portion in a retracted, unextended position. The device 20 is removably attached to the atomizer nozzle 21 by a friction fit between the nozzle 21 and the inner tube 24 of the device. Alternatively, an attachment means such as a detent rest or detent on the inner tube 24 can be employed to matingly engage a detent rest or detent on the nozzle 21 of a prior art dispenser as shown in FIG. 5 and 13. The eye cup portion 29 of the device is generally characterized as a hollow hemi-ellipsoid having an open elliptical end 27a having a skin-contacting rim 27b and a circular open end 27c opposite thereto. The eye cup portion 29 may be either removably attached to or permanently affixed to the outer tube 23 at the base 29 of the eye cup portion 11. The base 28 of the inner tube 24 is tapered on its inner surface to matingly conform to the tapered contour of the outer surface of the (prior art) dispenser nozzle 21. The mating engagement between the base 28 of the inner tube and the delivery nozzle 21 provides sufficient friction to prevent accidental disengagement of the device 20 from the nozzle 21. The skin-contacting rim 27b of the eye cup 29 is shaped to conform to the soft tissue surrounding the eye and to serve as a directional guide, as well as a seal, during delivery of a spray mist to the eye. The eye cup margin or rim 27b is preferably thicker than the wall of the eye cup 29 presenting a round, smooth, comfortable surface to the tissue surrounding the eye.

On the from surface of the eye cup 29 are two vent holes 26. These holes serve to relieve air pressure on the cornea of the eye which pressure may be created during the placement or removal of the device against the infra-orbital tissue. The spray containment chamber 25 is a (preferably molded) member shaped as the frustum of a cone and having means at the containment chamber's small diameter (distal) end for removable attachment to the interior of the eye cup 29 at its circular base. The purpose of the containment chamber 25 is to confine the delivery of the spray mist into a solid angle so that the mist may be delivered primarily to the cornea of the eye rather than to the general orbital area. The device 20 can be used to deliver fluid to the eye either with or without the spray mist chamber 25.

Figure 3:
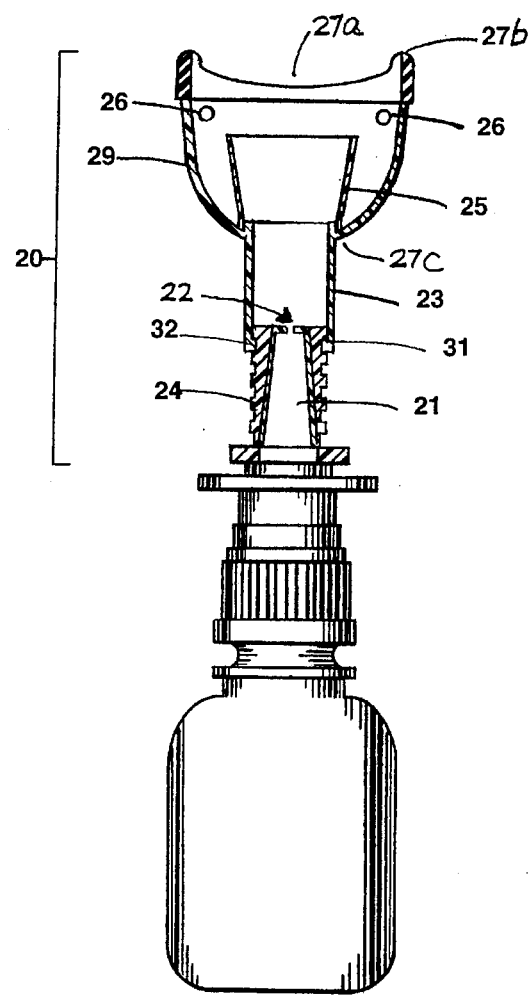
FIG. 3 shows the device in accordance with FIG. 2 with the outer tube of the tube portion fully extended with respect to the inner tube.

In FIG. 3, the end of the outer tube 23 to which the eye cup is attached is shown fully extended with respect to the base 28 of the inner tube. The inner tube 24 of the device 20 is removably seated on, and in mating engagement with, the (prior art) delivery nozzle 21. The interior cylindrical surface of the wall of the inner tube 24 is, as discussed earlier, tapered or otherwise shaped to conform to the exterior surface of the delivery nozzle 21 (prior art). The exterior surface of the inner tube 24 is cylindrical and dimensioned to slide within the outer tube 23. The maximum extension of the outer tube 23 is established by a travel limitation means such as a detent 31 on the outer surface of the inner tube 24 engaging a detent rest at 32 which may be a circular notch encircling the inner surface of the outer tube 23, to prevent further extension and disengagement of the inner and outer tubes.

Figure 4:
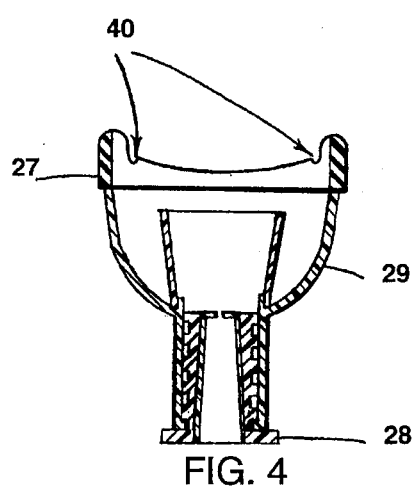
FIG. 4 is a partially cutaway side view of an alternate embodiment of the device showing vent slots in the eye cup portion.

An alternate embodiment of the device of FIGS. 2 and 3 is presented in FIG. 4 wherein vent slots 40 in the rim 27 of the eyecup 29 are used to prevent pressure from building within the eye cup in place of the vent holes 26 in the eye cup. The vent slots 40 are molded in the margin 27 of the eye cup and serve the same purpose as the vent holes 26.

A vertical cross-sectional view of a first embodiment of the device 10 of FIG. 2 which presents the main features representative of the present invention is shown in FIG. 5. In this embodiment 20, the inner tube 24 is shown mounted on a (prior art) atomizer nozzle 21. A portion of the outer surface of the inner tube 24 has a plurality of detent rests 51 arrayed thereupon. The detent rests 51 are preferably notches or similar indentations in the outer surface of the inner tube dimensioned to lockingly receive tabs 52 affixed to and projecting inward from the outer tube 23. The detent rests 51 and detent tabs 52 (shown in greater detail in FIGS. 5A, 8, 9 and 14), enable the intensity or dose of the spray mist delivered to the eye (or a portion thereof) to be reproducible by providing means for fixing the distance between the nozzle 21 and the rim 27 of the eye cup 20 for both comfort and accurate dosimetry. The outer tube 23 is shown fully extended and locked into position by flexible tabs 52, which are shown in greater detail in FIG. 8 and FIG. 9. In FIG. 5 and FIG. 5A, the base 28 of the inner tube 24 has a projection 28A extending upward to matingly engage a recess 28B (FIG. 9) in the base of the outer tube 23. This provides for the outer tube 23 to be properly positioned for extension, when required by the user. It also provides for the outer tube 23 to be properly positioned and locked in alignment for extension, when required by the user. It also provides for easier operation of the device by a user who has impaired vision or hand wrist coordination.

FIG. 5A is an enlarged view of the inner tube 24 showing the detent rests arrayed along the length of the outer surface of the inner tube. Detent rest 51, which receives the detent 52 (the flexible tab at the base end of the outer tube 23 shown in FIG. 9 at 52), serves four functions as shown in FIG. 14. The abrupt shoulder of the detent rest 51 prevents the accidental downward (collapsing) movement of the outer tube 23. The incline plane 51A portion of the detent 51 allows vertical movement when further extension of the device is required. The horizontal or lateral incline planes 51B and 51C provide means for the sliding, reversible disengagement of the flexible tab detents 52 from the detent rests 51 by the user by manually rotating the eye cup and the outer tube 23 relative to the inner tube. This rotation brings the flexible detent tabs 52 out of the notches and into contact with a portion of the inner tube having a smooth outer surface 100 (FIG. 11) so that the outer tube 23 can slide freely in relation to the inner tube 24. When the device is fully extended as shown in FIG. 5 and FIG. 5A, the detent 52 engages the upper most travel limiting detent rest on the inner tube 24. This terminal detent rest is different from the others inasmuch as it does not permit further extension there beyond. All other features of this detent rest are the same; including the release feature of the flexible detent tabs 52 from the detent rest by rotation of the eye cup which is affixed to the outer tube 23. As mentioned above, such a rotation causes the flexible detent tabs to ride up and out of the detent rest and brings the tabs into contact with the smooth outer surface 100 of the inner tube 24. In this position, the outer and the inner tubes may be moved telescopically for retraction or extension. section line 11—11 of FIG. 10 with the flexible detent tabs 52 seated in the detent rests. FIG. 12 provides a cross-sectional view of the inner tube 24 and the outer tube 23 with the flexible detent tab 52 engaging a detent rest at 111. The spaces 110 at the right and the left of the flexible detent tab 52 and the lateral incline spaces 51B and 51C as shown in FIG. 14 permits the fine adjustment of the eye cup either to the right or to the left when it is brought into contact to the orbital area. This adjustment feature is important in order to accommodate those users who might have a problem with the hand wrist coordination or some other physical limitation.

FIG. 8 shows the flexible detent tab 52 at the nozzle end of the outer tube. FIG. 9 shows a saggital of the flexible detent tabs 52 on the outer tube in an unstressed condition: that is, as they appear when the inner tube wall is not pressing on the detent tab, showing a slight deflection inwardly so that the internal ridges of the flexible detent tabs 52 will engage and seat within the detent rest, as the tabs slide along the outer surface of the inner tube 24.

FIG. 13 shows cross section of the inner tube 24, at its base areas and detents at 112 to secure the inner tube in place to the base of the delivery tube 21, detent rest not shown (prior an).

Returning now to FIG. 6 which is a cross-sectional view of the spray mist chamber 25, a further embodiment is shown. FIG. 6A shows an embodiment of the containment chambers having an elliptical eye-facing open end to conform to orbital area 19. FIG. 7 shows the base of the spray mist chamber 63 to be cylindrical in shape. In FIG. 6, the wall 61 of the spray mist chamber is seen to diverge, the open end 64 terminating into either an elliptical shape as shown in FIG. 6A or a circular shape. Changing the shape of the containment chamber creates a greater or smaller internal space 65 for confining the spray mist as it fans out before it reaches the eye area.

The tube portion of the device can be telescopically retracted to its most compact position, placing the spray nozzle at the nearest position to the eye. When the tube portion is completely retracted, the outer tube is rotated until an indentation on the nozzle end of the outer tube engages an indexing tab projecting from the base of the inner tube. This locating and locking device serves to position the outer tube in alignment so that when extension of the tube position is required, the flexible detent tabs 52 will be in the correct position to engage the notches or similar detent rests on the outer surface of the inner tube. This automatically places the assembly in alignment for extension.

The device is preferably sterilizable and compact for portability. The eye wash solution reservoir, if the device is permanently affixed to and an integral part of, a fluid mist dispenser is preferably small and refillable. The portable, compact unit is ideal for users who require frequent eye hydration, for home use, a larger version utilizing the same basic principles of design of the smaller portable unit but having a larger eye wash reservoir may be preferable.

Cleanliness of the eye spray mist dispenser device is of the utmost importance to prevent introducing foreign matter such as dust particles, and other debris into the eye. The most important concern is preventing any pathogens, including fungi, yeast, bacteria and viruses from contaminating the solution and/or the mist contacting surfaces of the device which could cause an infection of the eye. The user should take certain precautions to keep the eye spray mist dispenser device clean and free from contaminated material. Care should be exercised to prevent the fingers from touching the orifice of the dispenser nozzle. Rinsing the device with water before and after use is recommended. At intervals, a more complete maintenance should be done by a disassembly of the component parts so each could be cleaned separately. The device is preferably stored in a dust proof container.

There is a large segment of the population that suffers from dry eye syndrome and require frequent eye hydration. Such individuals require treatment a number times a day to attain an acceptable degree of eye comfort and the device described herein above is particularly useful for such people.

While particular embodiments of the present invention have been illustrated and described, it would be obvious to those skilled in the art that various other changes and modifications can be made without departing from the spirit and scope of the invention. It is therefore intended to cover in the appended claims all such changes and modifications which are within the scope of this invention.

What we claim is:

1. A device operable for controlling the delivery of a fluid mist discharged from the ejection nozzle of a spray mist dispenser to a person's eye comprising:

(a) a hollow hemi-ellipsoidal eye cup having a substantially elliptical proximal open end dimensioned to encircle a person's eye and having a skin-contacting rim on said open end contoured to anatomically conform to infra-orbital tissue adjacent to the person's eye and a distal circular open end;

(b) an axially adjustable tube portion comprising a cylindrical outer tube concentrically overlying a cylindrical inner tube, and having an axial mist-conducting lumen coextensive therewith, said outer tube having a proximal end attached to said eye cup to provide fluid communication between said mist-conducting lumen and said distal circular open end of said eye cup and a distal end, said inner tube being slideably disposed within said outer tube and having a proximal end and a distal end, said distal end of said inner tube including attachment means adapted to releasably attach to the nozzle of the spray mist dispenser, said mist-conducting lumen providing a conduit having an adjustable axial length operable for conducting a fluid mist from said distal end of said inner tube to said proximal end of said outer tube.

2. The device of claim 1, wherein said proximal end of said outer tube of said tube portion is rigidly affixed to said circular open end of said eye cup.

3. The device of claim 1 wherein said tube portion further comprises locking means operable for releasably locking said telescopically adjustable tube portion at a preferred length.

4. The device of claim 1 wherein said eye cup further includes a flow channel operable for conducting gas therethrough releasing excessive pressure within the eye cup when said proximal end and said distal end of said eye cup are occluded.

5. The device of claim 2 wherein said eye cup further includes means operable for maintaining ambient pressure within the eye cup when said proximal end and said distal end of said eye cup are occluded.

* * * * *